United States Patent
Zamanzadeh et al.

(10) Patent No.: US 7,678,253 B2
(45) Date of Patent: Mar. 16, 2010

(54) ATMOSPHERIC CORROSION SENSOR

(76) Inventors: Mehrooz Zamanzadeh, 1411 Grandview Ave., Apt. 510, Pittsburgh, PA (US) 15211; P. Richard Warburton, 1619 Ridge Rd., Moon Township, PA (US) 15108

( * ) Notice: Subject to any disclaimer, the term of this patent is extended or adjusted under 35 U.S.C. 154(b) by 1621 days.

(21) Appl. No.: 10/912,198

(22) Filed: Aug. 6, 2004

(65) Prior Publication Data
US 2005/0034985 A1      Feb. 17, 2005

Related U.S. Application Data

(60) Provisional application No. 60/493,776, filed on Aug. 11, 2003.

(51) Int. Cl.
  *G01N 27/26* (2006.01)
(52) U.S. Cl. .............. 204/431; 205/779.5; 205/781; 422/83; 422/96
(58) Field of Classification Search ............ 204/424, 204/431, 426, 779.5, 781, 404; 205/779.5, 205/781, 734; 422/83, 98
See application file for complete search history.

(56) References Cited

U.S. PATENT DOCUMENTS

| | | | | |
|---|---|---|---|---|
| 4,049,503 A | * | 9/1977 | Becker et al. | 205/779.5 |
| 4,129,479 A | * | 12/1978 | Morrow | 205/780 |
| 4,406,770 A | * | 9/1983 | Chan et al. | 204/406 |
| 5,250,171 A | * | 10/1993 | Warburton et al. | 205/783 |
| 5,746,899 A | * | 5/1998 | Finbow et al. | 204/415 |
| 6,191,696 B1 | * | 2/2001 | Young et al. | 340/632 |

OTHER PUBLICATIONS

R.S. Glass et al., U.S. Patent 5,306,41 (Apr. 26, 1994) Corrosion sensor that detect presence of corrosive species, as does the present invention, but via a different mode of operation.
R.S. Glass et al., U.S. Patent 5,437,773 (Aug. 1, 1995) Corrosion sensor that detect presence of corrosive species, as does the present invention, but via a different mode of operation.
P. Jaeger, U.S. Patent 6, 564,620, (May 20, 2003) Corrosion sensor that responds to a change in resistance as does present invention, otherwise operating principle is different.
E. Udd, U.S. Patent, 6,144,026, (Nov. 7, 2000) Example of modern corrosion sensor, optical fiber principle.
L. Yang, U.S. Patent 6,683,463, (Jan 27, 2004) Yang and the present invention both describe electrochemical corrosive gas sensors, but operating principle is different.

* cited by examiner

*Primary Examiner*—Nam X Nguyen
*Assistant Examiner*—J. Christopher Ball
(74) *Attorney, Agent, or Firm*—P. Richard Warburton

(57) ABSTRACT

An electrochemical sensor for corrosive gases that contains at least two electrodes is described. The presence of a target corrosive gas results in the formation of metal ions that can be reduced at an electrode producing an electrical current that depends on the instantaneous corrosive gas concentration and deposition of the metal on the electrode. Extension of this deposit to a second electrode through further deposition will result in a short circuit, the longer the time to the short circuit, the lower the cumulative corrosive gas concentration.

18 Claims, 2 Drawing Sheets

Amendments to Figures

ATMOSPHERIC CORROSION SENSOR

RELATED PATENT APPLICATION

This application claims the benefit of U.S. Provisional Application No. 60/493,776, filed Aug. 11, 2003 and entitled "Atmospheric Corrosion Sensor".

FIELD OF INVENTION

This invention is an electrochemical sensor used to measure the corrosive potential of atmospheric gases

BACKGROUND OF INVENTION

The refining of metals from their ores in a very energy intensive process and most metals in common use, e.g. aluminum, zinc, iron and their alloys etc. are thermodynamically unstable with respect to their oxides. Under ambient conditions the oxidation of these metals is called corrosion and the corrosion processes are very dependent on the environment in which the metals are kept. For example, steel objects kept in a clean low humidity environment, such as is found in the southwest United States deserts have very low corrosion rates, whereas the same object placed in a humid marine environment may corrode much more rapidly. In addition to humidity, other factors are known to promote corrosion, including temperature, salts (e.g. the marine environment above) and corrosive gases.

The cost of corrosion is very high, it has been estimated that the cost is equivalent to 3 to 5% of the gross domestic product of industrialized countries or $300 billion for the United States in 1995 {P. R. Roberge "Handbook of Corrosion Engineering" McGraw-Hill, New York, 2000}. From a more practical perspective, many metal objects are used at locations different from where they are manufactured and may sometimes suffer damaging corrosion before even being put into service. Once in service, corrosion may still occur. A whole industry has been developed to measure and control corrosion processes and details can be found in standard texts such as 1) P. R. Roberge "Handbook of Corrosion Engineering" McGraw-Hill, New York, 2000 2) L. L. Sheir, R. A. Jarman, G. T. Burstein "Corrosion, vols. 1 & 2", $3^{rd}$ Ed., Butterwork-Heinmann Ltd, Oxford (1994).

One part of the corrosion monitoring arsenal are corrosion sensors, devices that can be placed on a potentially corroding object or in the environment of the object that either provides a real time measure of the corrosion rate or a measure of the propensity of the environment towards causing corrosion. Corrosion occurs in many different environments and so there are many different types of corrosion sensor.

Some of the techniques that have been applied towards developing corrosion sensors include:

a) Electrical resistance—as the sensing element is corroded, its electrical resistance increases providing a measure of the corrosion rate.

b) Inductive resistance—changes in the thickness as the sensing element is measured by changes in the inductive resistance of a coil embedded in the sensor, thus providing a measure of the corrosion rate.

c) Linear polarization resistance—an electrochemical technique in which a small potential perturbation is applied and the resulting current is measured. The slope of the potential vs. current curve is the polarization resistance, which provides a measure of the uniform corrosion rate.

d) Electrochemical impedance—EIS is a newer technique that in which a small alternating potential is applied and the resulting current analyzed to provide impedance and phase information. EIS provides a great deal of information about corrosion processes and the status of protective coatings, but the analysis is often complex.

e) Electrochemical noise is a newer technique that measures the electrical noise that is associated with some corrosion processes, such as pitting.

f) Hydrogen sensors: Hydrogen evolution is one of the two common cathodic processes in corrosion (the other is oxygen reduction) and so the presence of hydrogen gas is indicative that corrosion is occurring.

There are many other techniques for corrosion engineering and these can be found in standard texts such as P. R. Roberge "Handbook of Corrosion Engineering" McGraw-Hill, New York, 2000.

One important area of corrosion monitoring is atmospheric corrosion. It is well know that some environments are more corrosive that others. For example iron objects corrode significantly faster near a marine environment than when located in an inland rural area. Typical atmospheric species that promote corrosion are chloride salts (marine environment) and corrosive gases such as sulfur dioxide ($SO_2$), hydrogen sulfide ($H_2S$), hydrogen chloride (HCl) and oxides of nitrogen ($NO_2$, $N_2O_4$, NO) associated with industrial pollution, such as combustion processes from diesel or gasoline powered engines. Typically these compounds promote corrosion by providing an acidic environment, an electrolyte for corrosion cells and/or for dissolving protective oxide layers from metal surfaces.

For many objects it is important that they are not being exposed to a corrosive environment. For example, by the time that corrosion products are seen on an object with a decorative coating, the damage would already be done and it would be too late to apply remedial measures. Therefore it is important to provide early warning that the environment is potentially corrosive.

To this end several atmospheric monitors have been developed. For example Sandia National Laboratories recently developed an atmospheric corrosion monitor that measured the reflectivity of an optically thin metal mirror (10-30 nm) on the end of an optical fiber. As the metal is corroded or reactive species chemisorb, the reflectivity decreases.

Another method that has been developed is the corrosion fuse in which a small wire coil under tension is exposed to the corrosive atmosphere. Corrosion leads to the wire stretching or breaking which can be detected by a fiber optic or other means.

Gas sensors have been used to directly monitor the presence of corrosive gases. Since these sensors detect the gases directly, early warning of a potentially corrosive atmosphere can be provided. However, in most cases the concentrations of the gases are at low or sub part per million concentrations and the cost of commercially available gas sensors and associated instrumentation is prohibitive for many applications. These and some other methods of corrosion monitoring are described in P. R. Roberge "Handbook of Corrosion Engineering" McGraw-Hill, New York, 2000.

BRIEF SUMMARY OF INVENTION

The present invention provides a low cost sensor for monitoring the local atmosphere for its propensity for promoting corrosion of metallic objects. In the first embodiment of the invention, a sensor is constructed of two or more closely spaced metal electrodes on a substrate electrical connected via an electrolyte, with a constant electrical potential applied between them. In the presence of a corrosive gas, corrosion of one of the electrodes releases metallic ions into the electrolyte. These ions migrate to the opposing electrode whereupon they are reduced back to the metal. Upon prolonged exposure to the corrosive gas, the deposited metal forms a metal bridge eventually resulting in a short circuit between the two electrodes. The corrosion tendency of the atmosphere is measured by both an instantaneous measurement of the current flowing between the two electrodes and by the time taken for the deposited metal to bridge the two electrodes. This current measurement provides a measure of the resistance between the two electrodes.

In another embodiment of the invention a sensor is again constructed from two closely spaced metallic electrodes, but the electrolyte contains an insoluble metal salt. A constant electrical potential is applied between the two electrodes. This metal salt is chosen such that exposure of the salt to acidic or other corrosive gases results in formation of a soluble metal salt. In the presence of a corrosive gas, corrosion of one of the electrodes (anodes) releases metallic ions into the electrolyte. These ions are transported by diffusion and/or migration to the negative electrode (cathode) whereupon they are reduced to the metal. Upon prolonged exposure to the corrosive gas, the deposited metal forms a metal bridge eventually resulting in a short circuit between the two electrodes. The corrosion tendency of the atmosphere is measured by both an instantaneous measurement of the current flowing between the two electrodes and by the time taken for the deposited metal to bridge the two electrodes.

In another embodiment of the invention the sensor is comprised of two or more essentially parallel and co-planer electrodes, with the electrolyte between them. The upper most electrode is porous and is covered with a porous hydrophobic membrane. The gas diffuses through the porous membrane and the upper porous electrode whereupon its reacts with the electrolyte. The reaction produces soluble ions that subsequently react at one of the electrodes producing a measurable electric current. Cumulative reaction at the electrode may also result in the formation of a conductive bridge between the electrodes. The time for this bridge to form provides a measure of the cumulative exposure of the sensor to the corrosive gases.

In a further improvement of the above embodiments of the invention, a small alternating electrical potential is also applied to the sensor. The resulting alternating current is measured and is used to provide a measure of the conductivity of the sensor. This conductivity can be used to provide a measure of condensation due to humidity and can also be used to detect the formation of the conductive bridge between the electrodes.

In a further embodiment of the invention, the electrodes may be selected so as to produce a galvanic cell within the sensor. This embodiment would allow the sensor to operate without external power being applied; instead it would be powered by the electrochemical reactions of the electrodes in manner analogous to a battery. The detection mechanism of the corrosive gases is otherwise similar to the methods described herein.

DETAILED DESCRIPTION

Figure 1:
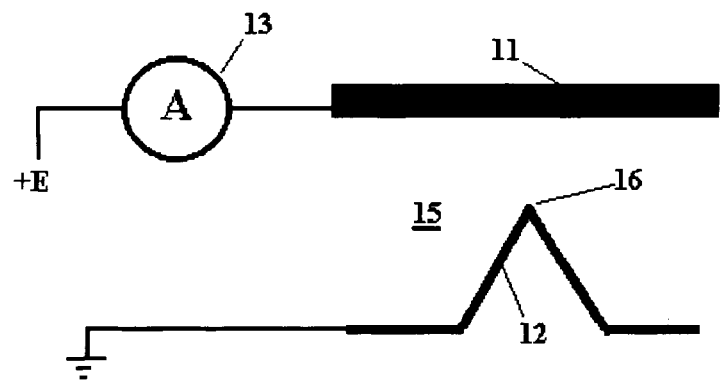
FIG. 1 Drawing showing key features of two electrode sensor cell

As described in above there is a great need for an efficient and economical system for monitoring for the presence of corrosive gases. The most common corrosive gases encountered are sulfur dioxide ($SO_2$), hydrogen sulfide (H2S), nitric oxide (NO), nitrogen dioxide/dinitrogen tetroxide ($NO_2$/$N_2O_4$) and hydrogen chloride (HCl). These compounds are the most important, but many other corrosive gases also exist and so it would be beneficial for a new gas detection system to be adaptable to other corrosive gases as well. Examples of other corrosive gases include ammonia and amines, hydrogen fluoride, silicon tetrachloride, acetic acid.

Corrosive gases can be grouped by their chemical properties, some gases are acidic, i.e. they form acidic solutions in water, such as sulfur dioxide, sulfur trioxide, hydrogen chloride, oxides of nitrogen, etc. Some gases are basic, for example ammonia and amines. Some gases are reducing, such as hydrogen sulfide and mercaptans. Some gases are oxidizing, such as chlorine, bromine, chlorine dioxide, ozone. Some gases are form ionic solutions in water, such as hydrogen chloride and some gases coordinate to metal ions such as ammonia and hydrogen chloride. As is evident from the few examples above, many gases are in more than one category and can promote corrosion in more than one way. The gases listed herein are representative only and as will be obvious to anyone experience in the art of gas sensor design, the present invention can be readily adapted to detect the presence of many other types of gases as well. These gases are the target gases for this sensor when it is necessary to detect their presence in air.

Most of the common corrosive gases have several features in common. They are acid gases, meaning that dissolution of these gases into pure water will produce an acidic solution (pH<7), and in the solution these gases will react with bases such as sodium hydroxide to produce salts. In addition dissolution of these gases in pure water will produce an ionically conductive mixture due to ionization of the gas. The following represent some of the possible reactions that are believed to occur:

Hydrogen chloride: $HCl \Leftrightarrow H^+ + Cl^-$

Hydrogen sulfide: $H_2S + H_2O \Leftrightarrow H^+ + HS^-$

Sulfur dioxide: $SO_2 + H_2O \Leftrightarrow H^+ + SO_3^-$

Nitrogen oxides: $2NO + O_2 \Leftrightarrow 2NO_2$ $2NO_2 \Leftrightarrow N_2O_4$ $NO_2 + H_2O \Leftrightarrow H^+ + NO_3^- + HNO_2$ This ability to form ionically conductive solutions is directly related to their propensity to support corrosion processes. Most metallic corrosion reactions are essentially electrochemical in nature and these gases promote the corrosion process by:

1) Adding an electrolyte to facilitate ionic charge transfer between cathodic and anodic sites,
2) Providing an acidic environment (high $H^+$ concentration)
3) Coordinating to metal centers and thus assisting in the degradation of otherwise protective oxide layers and
4) Possibly promote the oxygen reduction reaction in some circumstances ($NO_x$)

These properties of the gases that promote corrosion also provide the means for the detection of these gases. In many applications the instantaneous gas concentration is not as important as the cumulative exposure of the object being protected to corrosive gases.

The invention consists of an electrochemical cell with two or more electrodes and an electrochemically inactive electrolyte. For the purposes of this specification, an electrolyte is a material that contains ions that exhibit mobility; for example water with a dissolved salt, a solution of an acid or an alkali. This electrolyte may contain a rheology modifier, such as an organic polymer (e.g. polyethylene oxide, hydroxylethylcellulose) or and an inorganic (e.g. fumed silica), to control the flow characteristics of the electrolyte. The electrolyte may also contain a humectant, such as glycerol, hygroscopic or deliquescent compounds such as calcium chloride, to control the humidity balance of the electrolyte and thus control the resistance between the electrodes. For the purposes of this specification, resistance includes a measure of the electrical resistance of a material under either AC or DC conditions; thus resistance is the inverse of conductance. One embodiment of this invention is shown in FIG. 1. The cell is preferably, but not necessarily, constructed on a planar substrate with two electrodes 11 and 12 close to each other. The electrolyte 15 provides ionic electrical contact between the two electrodes, an anode 11 and a cathode 12 and essentially covers the space the between them. A constant, non-zero electrical potential (shown as +E) is maintained between the two electrodes by a conventional electronic circuit (not shown). This potential is chosen such that in the absence of a corrosive gas no electrochemical reaction occurs, but if the corrosive gas is present in sufficient quantity then an electrochemical reaction will occur. Varying this potential allows some changes to be made to the sensitivity of the sensor. If the potential is increased then the sensor is more susceptible to corrosion processes and so becomes more sensitive. Conversely if the potential difference between the two electrodes 11 and 12 is decreased then the sensor becomes less sensitive to the corrosive gases.

The substrate is preferably planar but can be other shapes and morphologies as well. The substrate should be electrically insulating and chemically inert. Otherwise the substrate properties will be determined by the other constraints such as being a suitable medium for deposition of the electrodes, cost etc. Examples of suitable substrate materials include alumina, silica, epoxy/fiber glass board and plastics.

The electrodes are preferably metallic and will be assumed to be herein, though non-metallic conductors (e.g. carbon) could in principle be used in some circumstances for the cathode. The choice of metal depends on the test requirements. Typically the metal used to prepare the electrodes may be chosen to have similar corrosion properties as the object being protected. Alternatively, the metal may be chosen to make the sensor more selective towards one gas over another. In one embodiment, the electrodes were formed from wires, e.g. threaded through holes in the substrate to both restrain the electrodes to the substrate surface and also to position them in the correct location. Alternatively, the electrodes may be formed directly on the substrate by a metal deposition method. These methods are well known in the prior art, for example the electrodes can be prepared using methods similar to those employed to make printed circuit boards, for example stencil printing and electrodeless deposition.

In its simplest form the sensor can contain two electrodes, namely the anode and the cathode. For this set-up the electronic drive circuit simply applies a constant potential between the two electrodes. Additional electrodes can also be used to improve performance. For example a reference electrode can be added to the sensor in order to isolate the effect of the potential drop at one electrode from changes in the potential drop at the other electrode. In this sensor the rate determining step (i.e. most critical to control) is the anode dissolution reaction. Therefore improved performance is obtained when the sensor contains a reference electrode and the electronic drive circuit is a potentiostat circuit with the anode as the working electrode. In principle, still better performance could be obtained by adding a fourth counter electrode thus enabling independent control of both the anode and cathode electrode potentials. A conventional bi-potentiostat circuit is used to drive this sensor. In practice however the increase in performance on going from a potentiostat to a bi-potentiostat circuit is small. The use of a reference electrode, potentiostat circuit and bi-potentiostat circuit are well known in the prior art and details can be found in standard electrochemical texts for example "Instrumental Methods in Electrochemistry, by the Southampton Electrochemistry Group, Publ. Ellis Horwood Ltd, Chichester, UK (1985).

The electrolyte also can be varied to change and control the properties of the sensor. In one embodiment of the invention the configuration is to have a water-based electrolyte free of salts, i.e. the electrolyte little to no electrical conductivity. Upon dissolution of the corrosive gas in the electrolyte, the gas is ionized providing the conduction means and thus providing means for the corrosion of the anode occur.

In another embodiment of the invention the electrolyte is preferably water based and contains a salt to provide ionic electrical conductivity. This salt should be chosen so that the metals used to fabricate the electrodes do not readily corrode in the absence of a corrosive gas as the operating potential. Examples of suitable salts include sodium, potassium or calcium salts of chloride, sulfate or hexafluorophosphate, though obviously there are many other salts, both inorganic and organic that could be used. The exact combination of salt and electrode material will need to be chosen based on the criteria described herein, and in light of the present disclosure this choice is within the capability of those experienced in the chemical arts, especially those with knowledge of corrosion processes.

Since the sensor is preferably formed on a planar substrate, it is preferable if the electrolyte contains a thickening/gelling agent to control the rheology of the electrolyte and also a humectant to ensure that the sensor can operate at low humidities as well as high. There are many of these so-called 'functional materials' available and their use is well known in the prior art. For example, suitable materials and suppliers are listed in standard references such as "McCutcheon's, Volume 2: Functional Materials, North American Edition, Published annually by McCutcheon Division, MC Publishing Co, Glen Rock, N.J.". The electrolyte may also contain chelating agents, such as ethylenediamine tetraacetic acid or its salts that will reduce the formation of protective oxides on the anode and thus promote corrosion. The combination of the electrolyte, anode material and the potential should make the anode much more susceptible to dissolution/corrosion processes that the object being protected so that the sensor will provide an early warning of a potential corrosive atmosphere.

The electrochemical reaction is dissolution of the anode 11 to form soluble metal ions and reduction of metal ions in the electrolyte to form a metallic deposit on the cathode 12. The metal ions that are reduced at the cathode 12 may be the same as the metal ions produced by the dissolution of the anode 11 or they may be different. The current flowing between the two electrodes 11 and 12 and in the external circuit can be measured by conventional means 13 to provide a metric of the rate of dissolution of the anode 11 and deposition on the cathode 12. Upon prolonged exposure to a corrosive gas the metal deposit on the cathode 12 will progressively grow until eventually it reaches the anode 11 thus providing a metallic short between the two electrodes 11 and 12. A larger current will not flow due to the applied potential and the sudden increase in current provides the indication that a shorting bridge between the two electrodes 11 and 12 has formed. It is preferable to have the electrodes 11 and 12 designed so that there is a definite narrow point between them. For example in FIG. 1, the cathode 12 has a kink that defines a point 16 that is closest to the anode 11. This kink thus ensures that the electric field strength between the anode 11 and the cathode 12 is greatest at the point 16, thus the deposition of the metallic deposit will occur at the point 16 rather than being dispersed along cathode 12.

The time taken from when the sensor cell was initially placed into service to the time that the shorting bridge is formed is also measured by conventional means. The higher the cumulative exposure to corrosive gases the shorter the time required for the shorting bridge to form. Thus the time taken for the shorting bridge to form provides a simple measure of the corrosive propensity of the atmosphere that the sensor is exposed to. For example, if an object were being transported/stored in a sealed container, with an expected residence time of two months, one of these sensors could be installed. If the atmosphere is non-corrosive, then the shorting bridge will not form and the operator can be assured that the object being transported will not suffer significant corrosion in transit. If however, the atmosphere inside the container is corrosive, then the shorting bridge will form, an alarm activated and remedial action taken before significant damage has occurred to the object in the container.

Obviously there are many variations possible to this invention. For example the time required for the bridge to form will depend on the spacing between the two electrodes 11 and 12. If the spacing is larger, then the time required to form the bridge will be longer. Similarly, the time required for the shorting bridge to form will depend on the ingress rate of the target gas. The addition of diffusion barriers, such as porous or gas permeable membranes or an impermeable sheet with a hole drilled in it, in the gas path e.g. overlaying the electrodes is one commonly used method to control the ingress of gas into gas sensors; though other diffusion barriers may also be used.

It is well known that some metals are more susceptible to certain corrosive gases than others {U. R. Evans, "The Corrosion of Metals", Publ. Edward Arnold & Co., (1926) pp 152-157}. For example, copper is severely corroded in the presence of ammonia vapor, but iron, steel and zinc show minimal corrosion. Conversely copper shows only superficial corrosion in the presence of hydrogen sulfide but iron and steel suffer significant corrosion. If it is desirable to make the sensor specific towards a particular gas, then the anode can be made from a metal whose corrosion is enhanced by the target gas. Conversely it may be preferable to prepare the anode material from the same or similar material as the object being protected. Thus the sensor would provide a measure of the susceptibility to the object being protected to the environment in general without specific knowledge of the gases involved.

If the object to be protected was composed of a metal that was not readily electroplated, for example if it were made of aluminum, which is very electronegative metal and thus not amenable to electroplating from aqueous solution, then the metal deposited on the cathode 12 would have to be different from the metal dissolved from the anode 11. The deposited metal should be one that is easily electrodeposited, for example, copper or silver. Thus the electrolyte 23 adjacent to the cathode 12 will contain for example copper ions (such as copper (II) sulfate). However, copper ions can cause corrosion of some metal surfaces due to the formation of local galvanic cells. Therefore, it is necessary to have two separate electrolytes 22 and 23, one adjacent to the anode 11 and one at the cathode 12 (see FIG. 2). These electrolytes 22 and 23 will need to be in electrical (ionic) contact with each other, for example via a salt bridge, or ionically conductive membrane, such as Nafion (Du Pont Corporation trademark) 21. In addition, since it will no longer be possible for the shorting bridge to extend to the anode, either the rate of corrosion can be based on the current flowing between the electrodes 11 and 12 by conventional ammeter 25.

In addition to corrosive gases, other environmental factors, especially temperature and humidity can also affect the rate of corrosion. The method of treating the effects of temperature and humidity depend on the application. For some applications, such as those where the intention is to detect the presence of a corrosive gas it will be desirable to compensate for the effects of temperature or humidity. A sensor such as is disclosed herein would not be used in isolation, but rather would be incorporated into an instrument. Temperature can easily be measured using conventional devices such as thermistors, and thermocouples and compensation can be performed by the appropriate software as is well known in the art of environmental instrument design. Similarly humidity can readily be measured using humidity sensors which are well known in the prior art and compensation can again be applied by conventional means in the instrument software.

However for most applications the concern is to detect the presence of a corrosive atmosphere and identifying the molecular and environmental factors involved are of secondary importance. For example both humidity and temperature increase the rate of corrosion as do the corrosive gases discussed above, but often the overall propensity for corrosion is more important than knowing what caused the corrosion. Since both temperatures and humidity increase the rate of reaction with in this sensor, the sensor output inherently changes with environmental factors such as humidity or temperature in a way that parallels the natural corrosion processes of metallic objects. Thus for most applications, where general corrosion is the concern, temperature and humidity compensation are neither needed nor desirable.

The above sensor has an additional advantage in most gas sensors provide an instantaneous measure of the gas concentration. In the present invention, the gas dissolved into the electrolyte and may stay there. Thus a brief exposure to a high concentration of corrosive as may lead to residual corrosive gas or its byproducts remaining in the electrolyte. This situation is very similar to the surface of a metallic object whereupon exposure to a brief but high concentration of a corrosive gas may leave a residual amount of the corrosive gas or its byproducts remaining on the surface of the object. Again, this property allows the sensor to parallel the behavior of a metallic corroding object.

Figure 3:
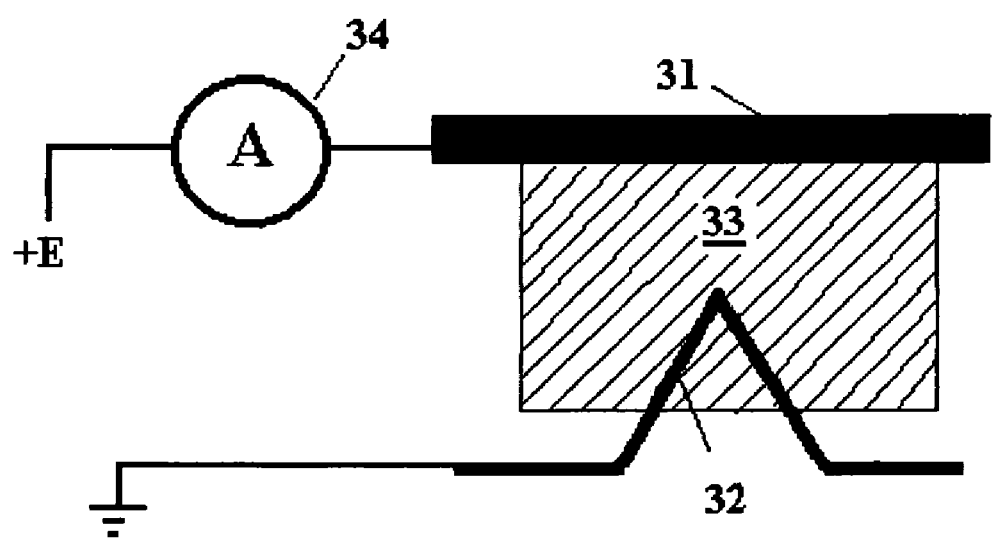

Another embodiment of this invention consists of a cell shown in FIG. 3 that is configured in a similar way to that described above and shown in FIG. 1. The cell shown in FIG. 3 employs a modified electrolyte to increase the selectivity to corrosive gases and decrease the effects of humidity. Instead of having the deposited metal ions (e.g. copper or silver) in solution, they are present as a solid or powder form of a metal salt intimately mixed with the electrolyte 33. The metal salt should be chosen with the following properties:

a) insoluble in water and the electrolyte b) reacts with the target corrosive gas to produce a soluble metal salt For example, if the electrolyte 33 contained copper carbonate or oxide or the silver analogues, then in the absence of the a corrosive gas at high or low humidity the free copper ion in solution would be very small and no metal would be deposited on the cathode. If the sensor in FIG. 3 were exposed to an acidic gas such as sulfur dioxide, then the sulfur dioxide would react with the basic copper carbonate in the electrolyte 33 to produce soluble copper bisulfite.

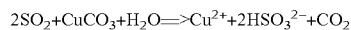

The copper (II) ions now in solution can migrate/diffuse to the cathode 32 and be reduced to copper metal. In addition to basic salts, other forms of immobilized metal ion can be used. For example, a high surface area copper alloy that readily corroded in the presence of the target gas could be used, e.g. present as a fine powder, or a copper deposited on a high surface area support, e.g. carbon. In addition to copper, other metals such as silver, lead and gold that can be electrodeposited on an electrode under ambient conditions.

Figure 2:
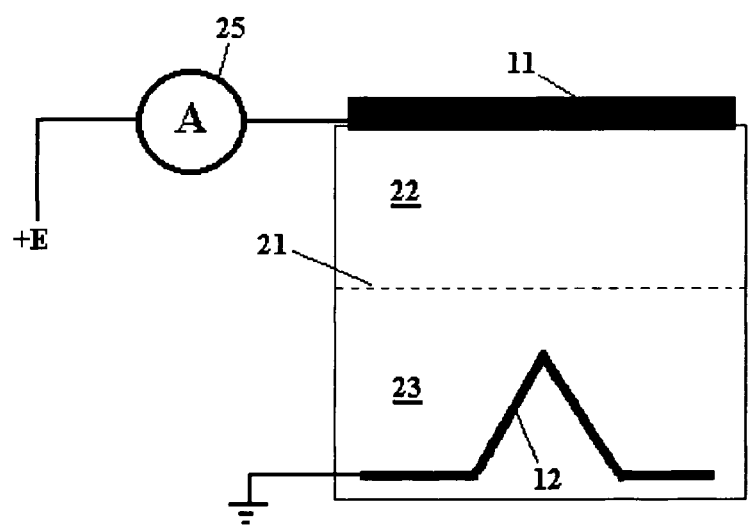
FIG. 2 Drawing showing key features of sensor cell with two different electrolytes FIG. 3 Drawing showing key features of two electrode sensor cell with gas responsive electrolyte

The cell configuration shown in FIG. 3 is generally similar to that in FIG. 1 or 2. The potential between the anode 31 and the cathode 32 is chosen as above to be such that in the absence of a corrosive gas there is not current, but in the presence of a corrosive gas there is an electrochemical process and hence a measurable electric current. This sensor configuration has the advantage that there is no current in the absence of a corrosive gas regardless of the humidity.

In the embodiments of the invention shown in FIG. 1 the selectivity of the sensor was determined by the anode material 11 and the rate determining step was the oxidation/dissolution of the anode material 11. The nature of the anode 31 in FIG. 3 is no longer as important as it was for the sensor depicted in FIG. 1 since the rate-determining step of the sensor reaction is no longer dissolution of the anode. The anode 31 in the sensor shown in FIG. 3 simply needs to be a material (not necessarily even a metal) that is easily oxidized. The rate-determining step is instead the reaction of the corrosive gas with the insoluble metal salt in the electrolyte 33. Thus the selectivity of the sensor can be tailed by merely changing the electrolyte 33. For example, if the sensor is intended to detect acidic gases then the electrolyte 33 should contain solid particles of a basic metal compound that will react with the acidic gas to form a soluble metal salt. Conversely if the target gas is a basic gas such as ammonia, then the electrolyte 33 should contain an insoluble compound that will form a soluble electroactive species upon reaction with the ammonia. The detection of the corrosive gas can be done in two ways as before. The current flowing through the sensor can be measured by conventional ammeter 34 or the time taken to form a shorting bridge between the anode 31 and the cathode 32 can be measured if applicable. The formation of the shorting bridge can be found by measuring the resistance across the cell (inverse of the current flowing at constant potential). Alternatively or additionally, if the first derivative of the current versus times is monitored, i.e. the rate of change of resistance with time), then the formation of the salt bridge can easily be detected.

In a further embodiment of the invention, the ions produced by reaction of the target gas with the solid or immobilized material within the electrolyte are such that they can be oxidized or reduced at the working electrode. The electrochemical potential of the working electrode is chosen such that this reaction will occur and the value chosen will depend upon the nature of the ion being reduced and the electrolyte composition. This ion can be a metal ion, such as cupric ion that is reduced to copper metal, but it could also be a non-metallic ion, for example it could a ferrous complex (e.g. ferrocyanide ion produced by reaction of hydrogen cyanide target gas with an insoluble iron (II) salt) that is oxidized to the corresponding iron (III) complex. It is advantageous to have the ion rendered electrochemically inactive upon oxidation or reduction at the working electrode, as occurs if the product is a deposited metal. However, other means can also be employed, for example, if the product is susceptible to selective absorption, then this absorbent can be added to the cell. For example, tethered or absorbed chelating agents can be used to selectively remove metals ions of a particular oxidation state. Alternatively, if the counter electrode material is chosen such that the kinetics of the counter reaction are kinetically hindered, then the counter reaction will not occur and the production of the working electrode electrochemical reaction is essentially rendered electrochemically inactive. A similar result occurs if the working electrode reaction is followed by a chemical reaction that leaves the product electrochemically inert. It is preferable if this product is either electrically conductive (e.g. a metallic deposit on the working electrode) or it is soluble in the electrolyte, in order to avoid blocking of the working electrode. The current will provide a measure of the target gas concentration and with modern microprocessors it is routine to track the current over time to calculate a cumulative exposure. By careful selection of the working, counter and optionally the reference electrodes, the electrolyte, the insoluble electroactive species bearing material; it is possible to design gas sensors that are specific to a given gas, or specific to a class of target gases. For example, if the insoluble material is a basic material such as copper oxide or copper carbonate, then the sensor will respond to acid gases. If the insoluble material contains a high surface area metal such as copper will respond to oxidizing gases. Thus by combining the wide variety of insoluble and soluble species known from in conventionally chemistry, it is possible using the present invention to design sensors with unique characteristics.

For all of the embodiments of this invention, it may be necessary to prevent some atmospheric species from reaching the sensor if they have an adverse effect. Adverse effects may include giving a large signal that swamps the signal from the intended target gas, or even damage to the sensor. Chemical filters can be employed with the sensor to increase the specificity to the target gas and to protect the sensor from potentially damaging gases. The use of chemical filters to protect sensors and improve their selectivity is well known in the art of gas sensor design.

For some gases measuring the time taken to form the shorting bridge between the anode 31 and the cathode 32 may not be applicable. If for example, the soluble compound produced upon reaction with the target gas with the insoluble particles in the electrolyte 33 were electroactive (i.e. it could be oxidized or reduced at either the anode or the cathode), but did not necessarily produce a solid deposit, then the current measured with conventional ammeter 34 would be sufficient signal for operation of the sensor.

We claim:

1. An electrochemical sensor for the detection of atmospheric gases or vapors, said sensor comprising an insulating substrate upon which are at least two electrodes, said electrodes closely space but not in contact with each other and the at least two electrodes are in contact with an electrolyte, containing a fluid medium that allows the movement of electrically charged ions, an external circuit that applies an electrical potential between at least two of the electrodes, a first electrode that is held at an electrical potential that is positive with respect to a second electrode, and the first electrode and at least part of the medium is exposed to the ambient air such that any target gases present in the air can reach and contact the first electrode and electrolyte, the first electrode being comprised of a metal that at least a component of which can be oxidized in the presence of a target gas so as to produce ions in the medium that are mobile and furthermore, the composition of said ions and the electrical potential are chosen such that said ions will be reduced at the second electrode so as to produce a metallic deposit in electrical contact with the second electrode; said sensor when in use is in contact with an external electrical circuit that maintain the potential between the first and second electrodes and monitors the resistance of the electrical pathway between the first and second electrodes such that the said circuit will provide an indication of the resistance of the path between the first and second electrodes and will provide an indication to the user if the resistance falls below a predetermined threshold.

2. A sensor of the type described in claim 1, wherein the target gas includes one or more of the following compounds: sulfur dioxide ($SO_2$), sulfur trioxide ($SO_3$), nitric oxide (NO), nitrogen dioxide ($NO_2$), dinitrogen tetroxide ($N_2O_4$), hydrogen chloride (HCl), hydrogen bromide (HBr), hydrogen sulfide ($H_2S$), chlorine ($Cl_2$), chlorine dioxide ($ClO_2$), bromine ($Br_2$), ammonia ($NH_3$) or a combination thereof.

3. A sensor of the type described in claim 1, wherein the target gas has one or more of the following characteristics—oxidizing gas, reducing gas, ionizing gas in aqueous solution, acidic gas or basic gas.

4. A sensor of the type described in claim 1, wherein the first electrode is comprised of copper, silver, an alloy of copper or an alloy of silver.

5. A sensor of the type described in claim 1, where in the electrolyte contains a rheology modifier.

6. A sensor of the type describe in claim 1, wherein the electrolyte contains a humectant.

7. An electrochemical sensor for the detection of atmospheric gases or vapors, said sensor comprising of an insulating substrate and at least two electrodes, said electrodes closely space but not in contact with each other and the at least two electrodes are in contact with an electrolyte, said electrolyte containing a fluid medium that contains a solid or immobilized material that will release mobile metal ions into the electrolyte upon exposure to the target gas, an external circuit that applies an electrical potential between at least two of the electrodes, a first electrode that is held at an electrical potential that is positive with respect to a second electrode, said ions and the electrical potential are chosen such that said ions will be reduced at the second electrode so as to produce a metallic deposit in electrical contact with the second electrode, said sensor when in use is in contact with an external electrical circuit that maintains the potential between the first and second electrodes and monitors the resistance of the electrical pathway between the first and second electrodes and will further provide an indication to the user if the resistance falls below a predetermined threshold value.

8. A sensor of the type described in claim 7, wherein the target gas is comprised of one or more of the following components: sulfur dioxide ($SO_2$), sulfur trioxide ($SO_3$), nitric oxide (NO), nitrogen dioxide ($NO_2$), dinitrogen tetroxide ($N_2O_4$), hydrogen chloride (HCl), hydrogen bromide (HBr), hydrogen sulfide ($H_2S$), chlorine ($Cl_2$), chlorine dioxide ($ClO_2$), bromine ($Br_2$), ammonia ($NH_3$) or a combination thereof.

9. A sensor of the type described in claim 7, wherein the target gas has one or more of the following characteristics—oxidizing gas, reducing gas, ionizing gas in aqueous solution, acidic gas or basic gas.

10. A sensor of the type described in claim 7, wherein the mobile ion produced upon exposure to the target gas is a copper ion or silver ion or a copper complex or a silver complex.

11. A sensor of the type described in claim 7, where in the electrolyte contains a rheology modifier.

12. A sensor of the type describe in claim 7, wherein the electrolyte contains a humectant.

13. An electrochemical sensor for the detection of atmospheric gases or vapors, said sensor comprising an insulating substrate and at least two electrodes, said electrodes closely space but not in contact with each other and the at least two electrodes are in contact with an electrolyte, said electrolyte containing a fluid medium that contains a solid or immobilized material that will release mobile metal ions into the electrolyte upon exposure to the target gas, an external circuit that applies an electrical potential between at least two of the electrodes, a first electrode that is held at a fixed electrochemical potential, said ions and the electrical potential are chosen such that said ions will be oxidized or reduced at the second electrode, said sensor when in use is in contact with an external electrical circuit that maintains the potential between the first and second electrodes and monitors the current flowing between the first and second electrodes.

14. A sensor of the type described in claim 13, wherein the target gas comprises one or more of the following components: sulfur dioxide ($SO_2$), sulfur trioxide ($SO_3$), nitric oxide (NO), nitrogen dioxide ($NO_2$), dinitrogen tetroxide ($N_2O_4$), hydrogen chloride (HCl), hydrogen bromide (HBr), hydrogen sulfide ($H_2S$), chlorine ($Cl_2$), chlorine dioxide ($ClO_2$), bromine ($Br_2$), ammonia ($NH_3$) or a combination thereof.

15. A sensor of the type described in claim 13, wherein the target gas has one or more of the following characteristics—oxidizing gas, reducing gas, ionizing gas in aqueous solution, acidic gas or basic gas.

16. A sensor of the type described in claim 13, wherein the mobile ion produced upon exposure to the target gas is a copper ion or silver ion or copper complex or a silver complex.

17. A sensor of the type described in claim 13, where in the electrolyte contains a rheology modifier.

18. A sensor of the type describe in claim 13, wherein the electrolyte contains a humectant.

* * * * *